(12) United States Patent
Schroeder et al.

(10) Patent No.: US 8,673,628 B2
(45) Date of Patent: Mar. 18, 2014

(54) METHODS AND APPARATUS FOR IMPROVING IN VITRO MEASUREMENTS USING BOYDEN CHAMBERS

(75) Inventors: Kirk S. Schroeder, Carmel, CA (US); Bradley D. Neagle, Ann Arbor, MI (US)

(73) Assignee: Essen Instruments, Inc., Ann Arbor, MI (US)

(*) Notice: Subject to any disclaimer, the term of this patent is extended or adjusted under 35 U.S.C. 154(b) by 63 days.

(21) Appl. No.: 13/157,873

(22) Filed: Jun. 10, 2011

(65) Prior Publication Data
US 2012/0315660 A1 Dec. 13, 2012

(51) Int. Cl.
C12M 1/34 (2006.01)
C12M 3/00 (2006.01)
B01L 3/00 (2006.01)

(52) U.S. Cl.
CPC .................................. B01L 3/5085 (2013.01)
USPC ..................... 435/288.4; 435/288.7; 435/29

(58) Field of Classification Search
USPC ...................................... 435/29, 288.4, 288.7
See application file for complete search history.

(56) References Cited

U.S. PATENT DOCUMENTS

| | | | |
|---|---|---|---|
| 5,601,997 A | 2/1997 | Tchao | |
| 6,270,730 B1 | 8/2001 | McLuen et al. | |
| 6,329,164 B1 | 12/2001 | Goodwin, Jr. | |
| 6,468,786 B2 | 10/2002 | Goodwin, Jr. | |
| 6,488,829 B1 | 12/2002 | Schroeder et al. | |
| 8,119,394 B2 | 2/2012 | McGrath et al. | |
| 2002/0123078 A1* | 9/2002 | Seul et al. | 435/7.2 |
| 2002/0185384 A1 | 12/2002 | Leong et al. | |
| 2004/0121432 A1* | 6/2004 | Klein et al. | 435/69.1 |
| 2004/0152067 A1* | 8/2004 | Wang et al. | 435/4 |
| 2005/0164404 A1 | 7/2005 | Marlborugh et al. | |
| 2009/0035745 A1* | 2/2009 | Shear et al. | 435/3 |

FOREIGN PATENT DOCUMENTS

WO WO-00/55298 9/2000
WO WO-01/32827 5/2001

OTHER PUBLICATIONS

Boyden, S., "The Chemotactic Effect of Mixtures of Antibody and Antigen on Polymorphonuclear Leucocytes" *J. Exp. Med.* 115: 453-466, 1962.
Frevert, C. et al., "Rapid fluorescence-based measurement of neutrophil migration in vitro," *Journal of Immunological Methods*, 213: 41-52, 1998.

(Continued)

Primary Examiner — Michael Hobbs
(74) Attorney, Agent, or Firm — Gifford, Krass, Sprinkle, Anderson & Citkowski, P.C.

(57) ABSTRACT

Apparatus and methods to improve the Boyden chamber used in cellular biological measurements, allowing quantitative optical microscopy of biological cells in situ without using fluorescent probes or optical staining. In the preferred embodiment, a thin porous membrane separating top and bottom reservoirs includes an array of precisely positioned micropores pores manufactured using a laser-based photo-machining (ablation) process. The membrane may be composed of polyethylene terephthalate (PET), polycarbonate, polyimide, polyether ether ketone (PEEK) or other appropriate material. The pores formed in the membrane may have diameters in the range of 1 to 15 microns and spaced apart at a distance ranging from 10 to 200 microns. A plurality of upper and lower reservoirs may be provided to form a multi-well plate. The invention finds application in a wide range of potential biological applications where Boyden chamber geometries are currently used including co-culture studies, tissue remodeling studies, cell polarity determinations, endocrine signaling, cell transport, cell permeability, cell invasion and chemotaxis assays.

27 Claims, 9 Drawing Sheets

(56) References Cited

OTHER PUBLICATIONS

Meyvantsson, I. et al., "Image-based analysis of primary human neutrophil chemotaxis in an automated direct-viewing assay", *Journal of Immunological Methods*, (2011 in press).

Quinn, J. et al., Model Pores of Molecular Dimension, the Preparation and Characterization of Track-Etched Membranes, *Biophysical Journal*, 12, 1972.

Sanyal, S. et al., Optimized Chemotaxis Conditions for Primary Blood Monocytes or THP-1 Cells using BD Falcon™ FluoroBlok™ 96-Multiwell Insert Plates, *Technical Bulletin #457, BD Biosciences*,, BD Biosciences-Discovery Labware, Bedford, MA 01730.

Zengel, P. et al., "u-Slide Chemotaxis: A new chamber for long-term chemotaxis studies," *BMC Cell Biology* 12:21, 2011.

\* cited by examiner

METHODS AND APPARATUS FOR IMPROVING IN VITRO MEASUREMENTS USING BOYDEN CHAMBERS

FIELD OF THE INVENTION

This invention relates generally to cellular biological measurement including cell migration (chemotaxis), cell invasion, cell permeability, tissue remodeling, cell polarity endocrine signaling and cell transport and, in particular, to apparatus and methods for improving the Boyden chamber apparatus used in such measurements.

BACKGROUND OF THE INVENTION

Cell migration is critical in many physiological processes. Chemotaxis, for example, is the study of cell motion in response to a soluble chemo-attractant stimulus. Similar and related mechanisms include haptotaxis and chemoinvasion, which rely on cell motility on a substrate-bound stimulus and movement through an Extracellular Matrix (ECM) boundary layer, respectively. These processes play a vital role in the study of many therapeutic areas including oncology, inflammation and angiogenesis. In recent years there have been many advances in the understanding of this physiological response, and much work has been done on the various classes of cytokines (e.g. TNFa, IL-1) and chemokine receptors (e.g. CCR2, CCR5).

Figure 1:
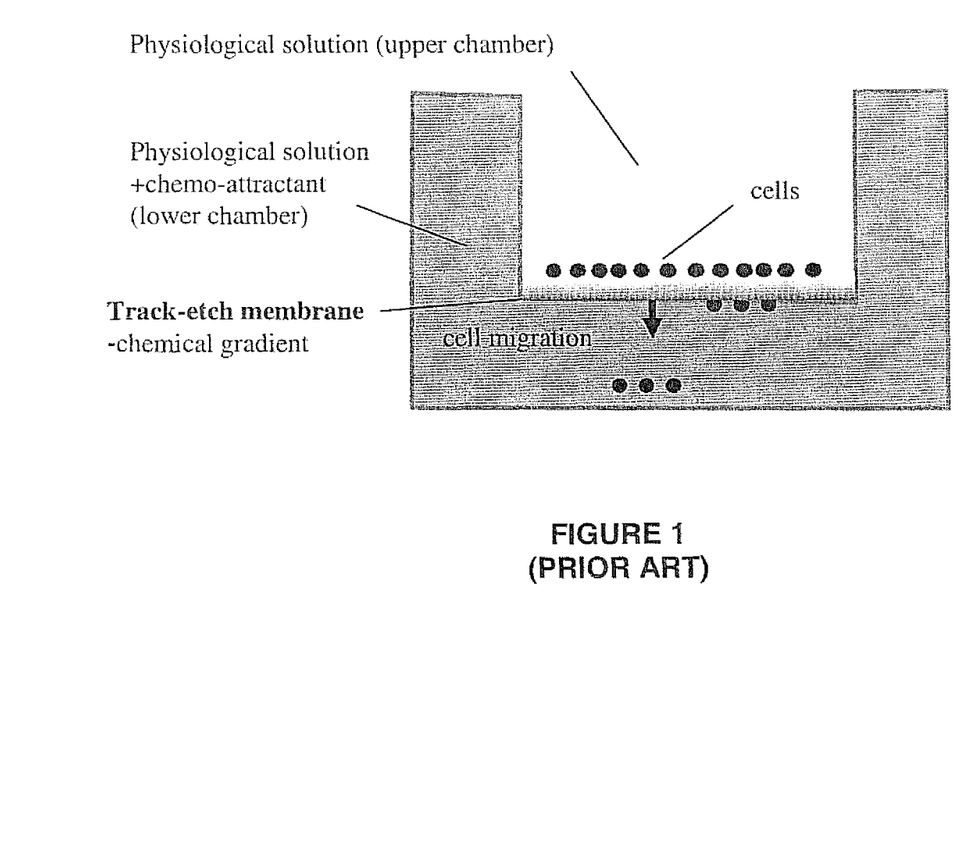
FIG. 1 depicts a single well of a prior-art Boyden chemotaxis chamber geometry.

The most common technique for measuring cell migration in vitro is via a measurement geometry known as the Boyden chamber [1] first described in 1962. This geometry, developed by Dr. Stephen Boyden consists of two chambers separated by a porous membrane as depicted in FIG. 1. When using a Boyden chamber as a chemotaxis measuring device, a chemoattractant is typically added to the lower chamber, cells are added to the upper chamber and the porous membrane serves as a means to establish a diffusion-based chemical gradient between the upper and lower chambers. The cells on the top side of the membrane detect this gradient, migrate to the individual pores in the membrane, and then crawl through the holes to the lower chamber. Once migrating through the pore, the cells ultimately either fall through the membrane to a lower reservoir, or end up migrating on to the bottom side of the membrane. Determination of the chemotactic response relies on quantifying the number of cells that migrated through the membrane in relation to the total number of cells added to the top chamber.

There have been many small improvements to the standard Boyden chamber geometry since its inception, but the basic device geometry and membrane components have remained fairly consistent. Currently, there are many commercial sources for 6-well, 24-well or 96-well. Boyden chamber-derived chemotaxis kits, including the ChemoTx™ system sold by Neuroprobe Inc. (Gaithersburg, Md.), the Transwell™ system sold by Corning Life Science (Acton, Mass.) and the HTS Fluoroblok™ system sold by Becton-Dickinson (Franklin Lakes, N.J.). All of these devices are basically rectangular arrays of Boyden chambers using microplate formats and injection mold fabrication techniques for the upper and lower reservoirs. All of these commercial devices also use the same basic material for the porous membrane which is known as a "Track-Etch Membrane".

Track-etch membranes are manufactured by exposing thin polymer films (e.g. polyester, or polycarbonate) to radioactive particle bombardment, followed by chemical etching [2]. The results of this manufacturing process are a thin film with a random pattern of very defined micro-holes as shown in the brightfield image of FIG. 2. The density of micro-holes using this fabrication technique is governed by the exposure time and exposure geometry in relation to the radioactive source. The size of the micro-holes in a given track-etch membrane is controlled by a combination of time, temperature and the chemical concentration used during the etch step. Typical etch solutions include highly concentrated NaOH, or HF. The micro-hole size is very uniform, and in general fairly orthogonal to the surface of the membrane. Pore size typically ranges from 0.2 microns, up to 10 microns in diameter. For filtering applications, it is generally better to have higher pore densities. However, due to the random nature of the ionization particle bombardment, pore density has a practical upper limit so as to avoid the random occurrence of "doublets", i.e. two pores touching each other. As such the "porosity" of track-etched membranes, defined as the area of pores divided by the area of non-pore, is generally on the order of a few percent.

The predominant application of such membranes is for fine particle and contaminant filtering of fluids as well a method of capturing and detecting microorganisms. The filtering applications take advantage of the very uniform and defined pore size of the membrane. This characteristic makes these types of membranes ideal for precisely filtering particles or microorganisms of a given size. For biological applications such as cell migration, track-etch membranes of 2, 3, 5 and 8 micron diameter pore sizes are most commonly used. For these applications, pore size is often matched to size of the cells being studied, bigger cells use bigger pores. Typically, the pore size is chosen to be slightly larger than the nucleus of the cells being studied. Most of the commercial manufacturers of Boyden-style chemotaxis chambers offer a variety of products incorporating different pore sizes. They also offer membranes in different materials, most commonly polycarbonate and polyester, and supply biological substrate coatings (e.g. collagen, fibronectin or laminin) or surface coating protocols. These biological coatings are sometimes useful so as to more accurately mimic the in vivo surface/adhesion biology of migrating cells.

The quantitative read-out from a Boyden chamber chemotaxis assay is based on a count of the number of cells which migrate through the membrane towards the chemoattractant in the lower chamber. Quite often, one must also employ negative control measurements where no chemoattractant is used in the lower chamber to correct for random migration effects. In existing commercial Boyden chamber technologies, quantification of the number of cells is accomplished by using fluorescent dye labeling of the cells. Labeling of the cells is necessary as the cells cannot be visualized on the surface of the track-etch membranes directly without using a fluorescent marker. Once labeled, the cells can be counted directly using cell counting microscopy; or if a proportionality relationship can be established between fluorescence and cell number, a bulk fluorescent measurement can be made which is proportional to cell number. Cells are typically labeled at the beginning of the experiment, i.e. before cell migration occurs. Cells can also be "post-labeled", i.e. after the cell migration occurs. This latter method is often preferred when working with time-sensitive or label-sensitive cell types.

Boyden chamber technology is the current "gold standard" for in vitro chemotaxis assays and has been around for almost fifty years. The modern incarnations of the technique have the advantage of being amenable to multi-well microplate formats and the precision of plastic injection molding techniques; as such they are fairly high throughput and reasonably priced. While being the current gold standard, and clearly dominating the research market, there are several disadvantages to the current Boyden chamber systems. These disadvantages will be discussed in the following paragraphs Disadvantages of Prior Art Boyden Chamber Geometry for Measuring Chemotaxis A. Temporal Variation of the Chemoattrant Gradient:

Because Boyden chambers rely on passive chemical diffusion in order for a gradient to be formed between the upper and lower reservoirs, there is no active control of the gradient process. The chemical gradient formed is simply a function of the pore size, time, concentration and the molecular weight of the chemoattractant. The gradient is, by definition, time varying and eventually the top chamber and bottom chamber chemical concentrations equalize and the gradient is destroyed. Not having the ability to modulate or control the time varying aspect is a disadvantage of this approach. In addition, because of the random spatial location of the pores formed by the track-etch process, the chemical diffusion gradient is also very non-homogeneous at the top surface of the membrane. Lastly, the transient and non-homogeneous nature of the chemical gradient using current methods can cause time-sensitive, and concentration cell migration responses. These in turn can cause artifacts where, depending on the timing and or concentration of the agonist, it is impossible to determine if a reduction in cell migration is due to a degradation of the chemical gradient, or the effect of an experimental pharmacological agent.

In recent years, researchers have designed and built chemotaxis chambers using microfluidic channels with the goal of establishing better defined chemical gradients as well as adding the ability to image the migrating cells directly. A few of these approaches have reached the commercial market [3,4]. These microfluidic approaches generally allow for a more quantified chemical gradient to be formed, offering the ability to characterize the formation and temporal characteristics of the gradient using fluorescent labeled molecules and fluorescent microscope detection. However, although the gradients are quantitatively characterized, none of the micro-fluidic approaches have eliminated the temporal and transient nature of the gradient formation and the potential artifacts this can cause.

Also, micro-fluidic devices work with small fluid volumes. As such getting fluids and living cells into micro-fluidic chambers is cumbersome, and typically researchers end up working with very small fluid volumes which are prone to evaporation effects. Physiological buffering agents can cause osmotic stress to living cells in the presence of even minor amounts of evaporation. The smaller the volumes utilized the more sensitive the effects of the evaporation can become. Another drawback of the micro-fluidic approaches is that they tend to provide very shallow chemical gradients, on the order of a percent or two of absolute concentration change across a cell diameter. It is generally believed that a cell requires at least a 2% absolute concentration difference across the cell diameter in order for the cell to respond in a directed manner. The concentration gradients achieved in microfluidic devices are on this order or smaller, as such the microfluidic solutions tend to be limited in their chemotactic efficiency (the number of cells which respond). So while there are some advantages to the microfluidic approaches, to date, none of the microfluidic-based commercial solutions has supplanted the Boyden chamber has the dominant "gold standard" measurement system for in vitro chemotaxis.

B. Current Techniques Require Fluorescent or Optical Dye Labeling to the Cells:

Quantitation of chemotaxis in a Boyden chamber geometry relies on fluorescently labeling the cells, either prior to the experiment, or after the experiment in a post-labeling step. The "signal" from a Boyden chamber chemotaxis assay relies on counting the number of cells that have migrated from the top side of the membrane through the micro-hole of the track-etch membrane. Once migrating through the pore, some cell types will adhere and migrate to the bottom side of the membrane. Other cell types will not adhere, and will fall through to a bottom collection chamber, typically a reservoir microplate. Cells are "counted" either by using a fluorescent microscope and "counting" individual cells on the bottom side of the membrane, or those in the bottom reservoir (or both). In some cases, a microscope is not used but rather a bulk fluorescent measurement is made using a fluorescent plate reader. This latter technique relies on establishing a fluorescent calibration curve between the fluorescent label used and the number of cells.

The practical impact of requiring a fluorescent label to effectively "count" the cells is a big disadvantage in running these types of assays. First and foremost, a lot of chemotaxis assays rely on using "primary" hematopoetic blood cells (e.g. T-lymphocytes, neutrophils) which are very sensitive to potential toxic effects of fluorescent dyes. Secondly using fluorescent or optical dye labeling techniques makes the assays more expensive as the labeling step and reagents cost time and money. Lastly, the presence of labels can make it is necessary to introduce non-homogeneous work-flow processing steps. For example, if the cells migrate to the bottom of the track-etch membrane, it may be necessary to manually remove or 'scrape" any remaining fluorescent cells from the top side of the membrane to avoid counting these cells as migrated cells. Any manual process like cell scraping takes more time, interrupts the workflow, thereby limiting assay throughput, and introducing dominant errors in the quantitation of the response.

Figure 3:
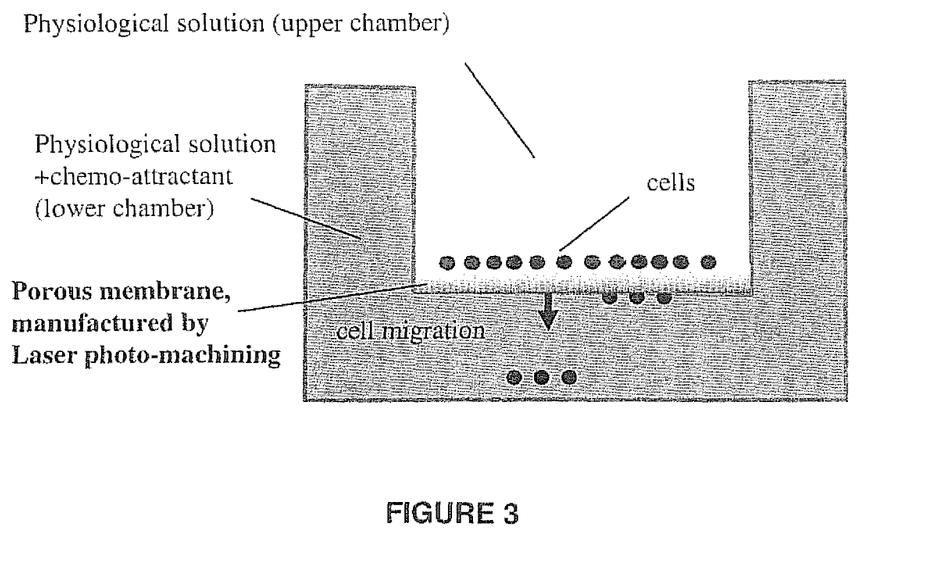
FIG. 3 illustrates a preferred embodiment of a Boyden chamber using a photo-machined membrane.

Biological cells are in general transparent, and rely on either fluorescent labeling to view or host of other techniques which encode subtle optical phase changes introduced by the cells into detectable intensity change. Imaging techniques which work on this premise include Zernike phase contrast, differential interference contrast (DIC) and Hoffman Modulation Contrast (Phase-Sensitive Techniques). Phase-sensitive imaging techniques rely on placing the cells on very high optical quality substrates such as thin glass slides or thin plastic substrates. It is not enough however, that the substrate be optically clear, it must also not introduce any significant phase perturbation to the optical wavefront which would distort or mask the subtle phase variations introduced by the biological cells. Phase-sensitive imaging is not amenable to the current commercially-available Boyden chamber consumables which rely on porous membranes manufactured by the track-etch manufacturing process. Membranes produced by the track-etch process introduce a variety of optical phase perturbations when imaged with a phase contrast microscope, making detection of the cells on the surface without using fluorescent labels or optical dyes/stains impossible as shown in FIG. 3. As such, commercially available Boyden chamber geometries are not amenable to direct cell viewing.

Cells undergoing migration take on many distinctive morphological phenotypes often denoted as "shape change". The ability to detect "shape change" as well as to validate the chemotactic signal that one is measuring during a chemotaxis assay without fluorescently or optically labeling the cells would be extremely beneficial. In fact, the ability to visualize the cells during the assay has been one of the key design motivations for the development of the micro-fluidic approaches aforementioned. Unfortunately this advantage has not overcome the disadvantages associated with relatively shallow chemical gradients and evaporation effects.

C. Number of Cells Required to Quantify the Response:

Another disadvantage of currently available Boyden chamber derived chemotaxis kits is that they require large number of cells to characterize the response, typically tens to even hundreds of thousands of cells per well. Large cell numbers can be a major cost/adoption disadvantage. This is especially the case when using rare, and perhaps difficult to isolate primary hematopoietic cells from the blood.

One reason that commercially available Boyden chamber technologies require large cell numbers per well, is that at any given concentration gradient, the actual "participation rate", i.e. the number of cells which may respond to the level of chemical gradient may be fairly small (e.g. a few %) of the starting number. In order for the experiment to result in a reasonable number of cells migrating through the porous membrane, one has to start with very large numbers of cells on the top side of the membrane. The dynamic range problem is further complicated in that often researchers are interested in finding compounds which inhibit the chemotactic response. The result is that a low signal level gets even smaller upon inhibition, thereby creating a small dynamic range ("signal window") for the assay.

Detection of very small cell numbers of migrating cells from the starting population is difficult to do with current commercial systems as it is not easy to image the various surfaces where the cells are located (top side of membrane, bottom side of membrane or lower reservoir). If using fluorescence, one must be able to separate fluorescent signal from the top side of the membrane from fluorescent cell counts from the bottom side of the membrane. This may require the need for time-consuming, manual assay steps such as "manual cell scraping", in order to separate the fluorescent signal on the top side of the membrane vs. the fluorescent signal on the bottom side of the membrane. These types of steps are prone to human error and variability and are greatly detrimental to the precision of a Boyden chamber chemotaxis assay.

To eliminate this problem, Becton Dickinson (BD) introduced the Fluoroblok™ technology in 1997 (U.S. Pat. No. 5,601,997). This invention introduced an optically-opaque barrier in the membrane, such that detection of the fluorescence from the bottom side of the membrane would not be sensitive to any fluorescently-labeled cells remaining on the top side of the membrane. This was a definitive advance in helping to remove manual preparation steps. Unfortunately, the Fluoroblok™ consumables are relatively expensive, the technique still requires fluorescent labels, it is not easy to image the cells or observe cell morphology and the systems require large numbers of cells per well. Assays using the BD Fluoroblok™ technology typically require 50,000 to 100,000 cells per well [5].

In summary, the Boyden chamber geometry remains the gold-standard measurements technique for measuring in-vitro chemotaxis. However, the commercial solutions for the Boyden chamber geometry all suffer from the following disadvantages:

1.) Time varying chemical gradient
2.) No ability to alter spatial pore geometry
3.) Require fluorescent probes or optical dyes of the cells to quantify the response
4.) Not amenable to viewing the cells in situ during the assay
5.) Require large numbers of cells Microfluidic chemotaxis assay designs have improved on the ability to directly image the cells, and have incorporated the ability to characterize the chemical gradient formation, however, they suffer from:

1.) Resulting chemical gradient is very shallow
2.) Detrimental evaporation effects, osmotic stress effects
3.) Are either extremely low throughput, or cumbersome to use

SUMMARY OF THE INVENTION

This invention relates to an apparatus and methods for improving the Boyden chamber used in cellular biological measurements. In accordance with the invention, cells can be directly imaged and analyzed in situ and without using fluorescent labels or optical dye staining. In addition, the pore spacing and pore diameter of the filter membrane can be precisely controlled, enhancing the use of the devices for chemotaxis and chemo-invasion type assays.

Apparatus constructed in accordance with the invention includes a bottom reservoir, a top reservoir, and a thin porous membrane separating the top and bottom reservoirs. In the preferred embodiment, the pores of the membrane are manufactured using a laser-based photo-machining (ablation) process.

The membrane may be composed of polyethylene terephthalate (PET), polycarbonate, polyimide, polyether ether ketone (PEEK) or other appropriate material with optical characteristics which do not introduce significant phase perturbation to an incoming light wavefront in relation to those introduced by biological cells on the surface of the membrane. The pores formed in the membrane may have diameters in the range of 1 to 15 microns and spaced apart at a distance ranging from 10 to 200 microns. A plurality of upper and lower reservoirs may be provided to form a multi-well plate.

The invention may be used for the measurement of cell migration (chemotaxis), cell invasion, cell permeability, tissue remodeling, cell polarity endocrine signaling or cell transport. In a common application the porous membrane is used to separate upper and lower fluid-containing reservoirs and coated with collagen 1, fibronectin, laminin or other extracellular matrix material. An inverted phase contrast, DIC, or Hoffman Modulation-type microscope may be used to assess the morphology and/or number of biological cells on the membrane. An advantage of the invention is that chemotaxis, cell migration, cell invasion and other processes may be carried out by counting the cells on the top surface of the porous membrane directly and without using fluorescent labels or optical dye staining.

The improvements made possible by the invention impact a great range of potential biological applications where Boyden chamber geometries are currently used including co-culture studies, tissue remodeling studies, cell polarity determinations, endocrine signaling, cell transport, cell permeability, invasion and chemotaxis assays. While the description presented here is intended to describe the advantages of the invention specifically as it relates to the measurement of in vitro chemotaxis and in vitro cell invasion assays, many of the attributes associated with the invention are extendable to other common uses of Boyden chamber systems.

DETAILED DESCRIPTION OF THE INVENTION

This invention is broadly directed to a process of manufacturing the porous membrane used in Boyden chamber design. Traditional track-etch membranes used in the production of commercially available Boyden chamber devices commonly used thin polymer films such as polycarbonate or polyethylene terephthalate (PET). The process of making pores in track-etch membranes involves bombarding the surface with radiation, typically alpha particles followed by a chemical etching step using highly concentrated NaOH or HF acid. The pore density (number of pores and density) is controlled by the physical geometry and exposure levels to the radiation source. The pore size is determined by the concentration and exposure time in the etch step. Unfortunately, the result of this process is a material that has significant optical surface blemishes. These blemishes prohibit the use of common non-labeled, non-invasive imaging techniques such as phase contrast, or differential interference contrast (DIC) to view cells on the surface of the membranes.

Figure 2:
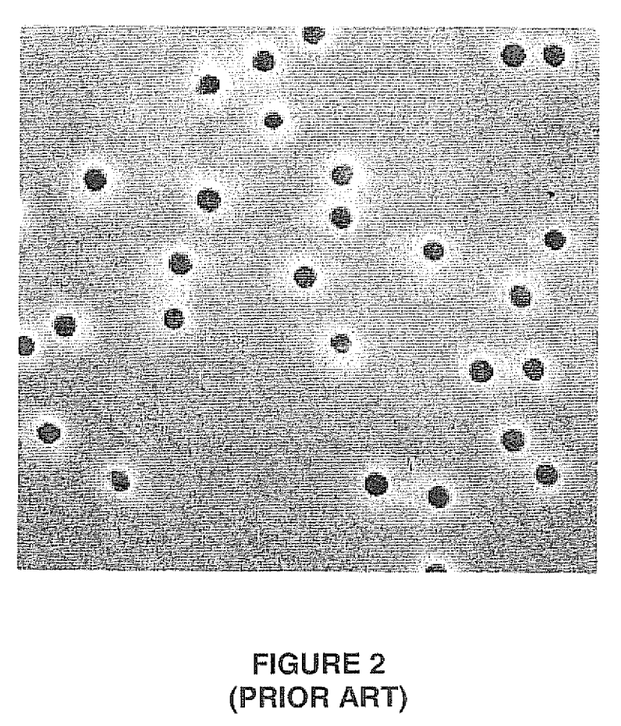
FIG. 2 shows a prior-art bright field image of a track-etch membrane surface.

FIG. 1 shows a Boyden Chamber single-well geometry for measuring cell migration utilizing a track-etch membrane filter. Migrating cells can either adhere to the lower side of the track-etch membrane, or fall through the membrane to a lower reservoir for detection. FIG. 2 is a bright-field image of a track-etch membrane. Micropores are random. One of the enabling aspects of the disclosed invention is the ability to precisely locate the individual micro-holes. Surface and material characteristics make non-labeled, phase contrast imaging of cells on the surface impossible. All that is visible without using fluorescent labels are the micro pores themselves.

The preferred embodiment of this invention resides in a porous membrane manufactured by a different manufacturing process, one based on laser-based photo-machining. Laser-based photo-machining generally uses a pulsed laser of the proper wavelength and pulse energy such that the optical energy is absorbed by the target material (in this case a thin polymer film) resulting is small pieces being ablated from the surface with each pulse. The laser beam can be precisely positioned in X-Y and the beam dimension, optical power and pulse repetition frequency can be precisely controlled so as to allow for very fine micro-hole machining. The goal is to provide a regular-spaced grid of micro-holes in a thin film whereby the pore density and pore size are carefully controlled and the resulting porous material has much improved optical surface characteristics in comparison to track-etch membranes (prior art).

FIG. 3 depicts one specific embodiment of the invention, where the track-etch membrane is replaced by photo-machined membrane. It is envisaged that much like current track-etch membranes, a variety of micro-hole sizes and densities could be utilized to optimize a measurement geometry for a particular cell type and assay. One of the advantages of this approach, is being able to control the precise location and density of the photo-machined micro-holes. This is in contrast to the random location of the microholes as provided with track-etch membranes (prior art).

Figure 4:
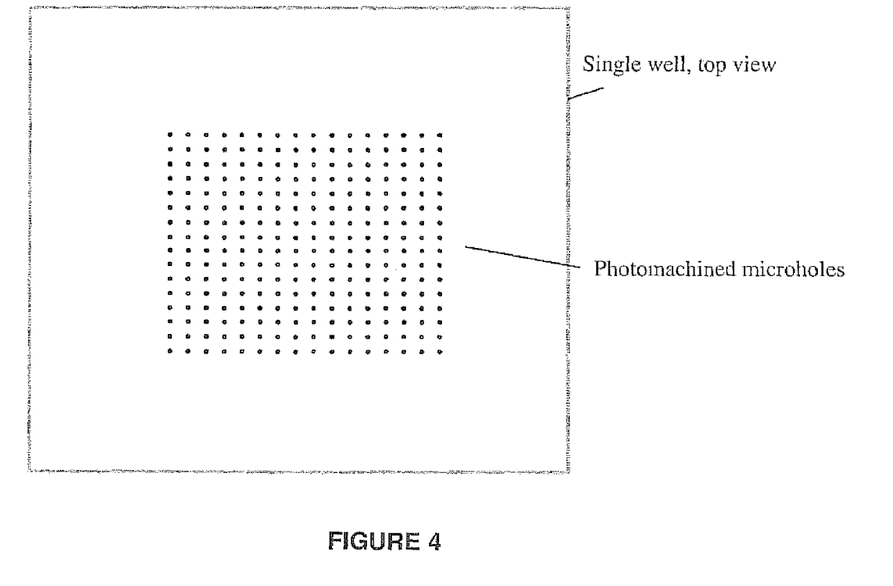
FIG. 4 shows a rectangular array of micro-holes forming the porous membrane of a Boyden chamber geometry.

For chemotaxis studies, it is often desirable to scale the size of the micro-holes in the membrane in proportion to that of the cells being analyzed. This scaling helps to alleviate the contribution of chemokinesis (random migration) to the measured chemotactic signal. Using photo-machining to make the individual micro-holes provides, for the first time, the ability to control the micro-hole density and spatial location. FIG. 4 is a specific example of a preferred embodiment using a 16×16 array of microholes, 8 uM in diameter and 60 microns apart. The specific dimensions shown here are only an example, demonstrating the fact that unlike the track-etch membranes, the pore density can be carefully controlled. Using this approach, one could design and implement many defined variations of micro-hole size and spatial density.

Figure 5:
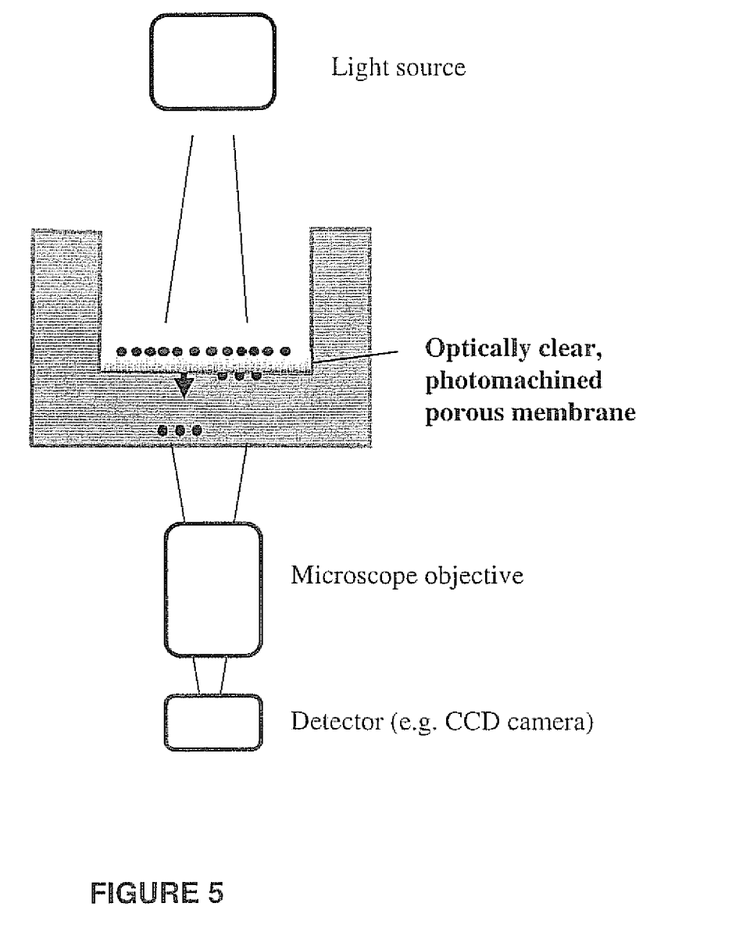
FIG. 5 is an inverted phase contrast imaging geometry for the improved Boyden chamber.
Figure 6A:
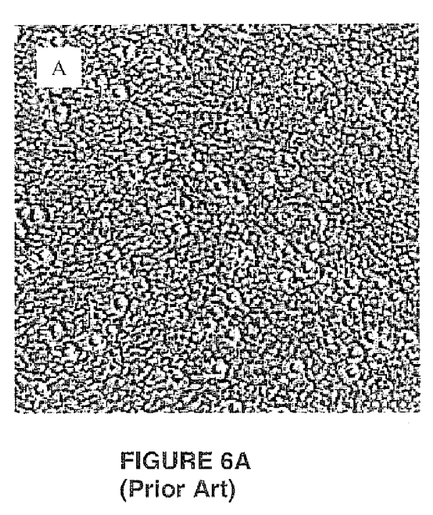
FIG. 6A illustrates a phase contrast image of a track-etch membrane (no cells)
Figure 6B:
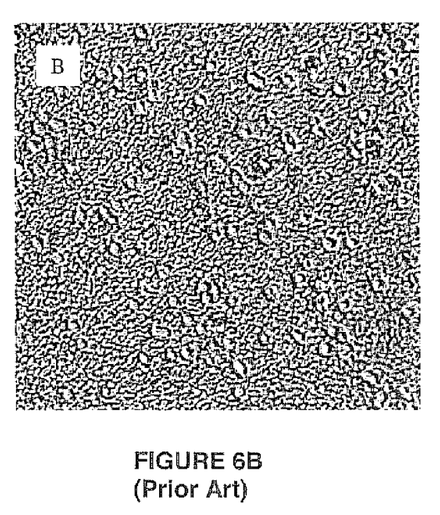
FIG. 6B illustrates a phase contrast image of a track-etch membrane (with cells)
Figure 6C:
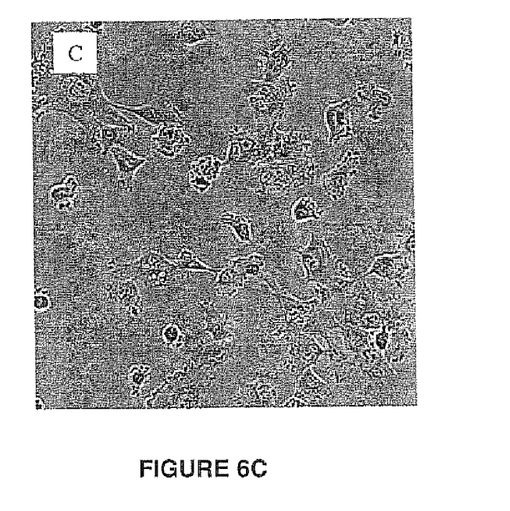
FIG. 6C illustrates a phase contrast image of cells on a high quality plastic substrate.

The ability to laser photo-machining (ablation) of the micro-holes to fabricate the porous membrane has many potential advantages. First and foremost, the photo-machining process is not detrimental to the optical quality of the thin film polymer material. Unlike the track-etch membrane process which requires a chemical etch of the entire surface to form the pores, the laser machining process has minimal detrimental impact on the optical quality of the film in the regions between the micro-holes. The laser machining process is local machining process, whereby some ablated material will be deposited around the hole, but this has very little detrimental effect on the optical quality of the polymer film in the area between the micro-holes. Maintaining a high optical quality substrate enables quantitative, high contrast morphological analysis and/or cell counting of individual living cells on the membrane without using fluorescent labels or optical dyes. This is a big advantage over current Boyden chamber methodology which requires fluorescent labeling to image and count the cells due to the poor optical characteristics of the track-etch membranes. FIG. 6A is a phase-contrast image of a prior art track-etch membrane. FIG. 6B is a phase contrast image of the track-etch membrane with cells on the surface of the membrane. Due to the optical perturbations caused by the membrane, quantitative imaging is not possible. FIG. 6C is a phase contrast image of cancer cells on a high quality optical substrate, tissue culture plastic in this example. FIG. 5 is an example of inverted of an inverted phase contrast method applied to a single well of a Boyden chamber geometry using a photo-machined membrane. Precise photo-machining of the thin polymer film leaves an optical surface free from aberrations and enables the use of phase contrast, or other non-labeled, imaging techniques for enumerating the cells on the membrane in situ. This imaging geometry cannot be used to quantitatively assess cell biology with current commercially available Boyden chamber solutions using track-etched membranes as the cells are not visible as demonstrated in FIG. 6C.

The ability to image the cells on the membrane directly has many potential benefits aside from being able to quantify cell migration without the use of labels. A non-labeled, homogeneous assay approach, is amenable to a kinetic, multiple time point read-out. Often, labeling of the cells precludes kinetic read-outs due to the fact that the cells are dye loaded after the cell migration is over, or if pre-loaded, the dyes can introduce phototoxicity upon repeated light exposure. Using a non-labeled approach eliminates manual intervention steps such as scraping cells off the top, or bottom side of the membrane in order to count them. These types of manual steps are prone to human error and subjectivity, and cause errors in the precision of the assay. Making the assay protocol homogeneous, allows for better assay controls, and in-turn should reduce the number of cells required to quantify the migration response.

Figure 7A:
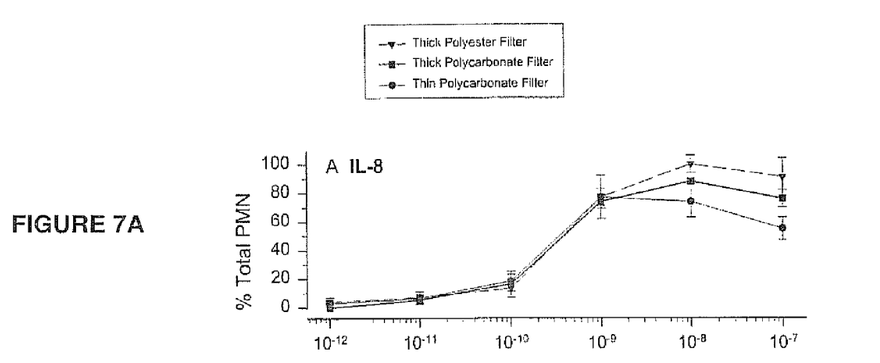
FIGS. 7A and 7B are graphs illustrating an agonist saturation effect for existing Boyden chamber chemotaxis assays.
Figure 7B:
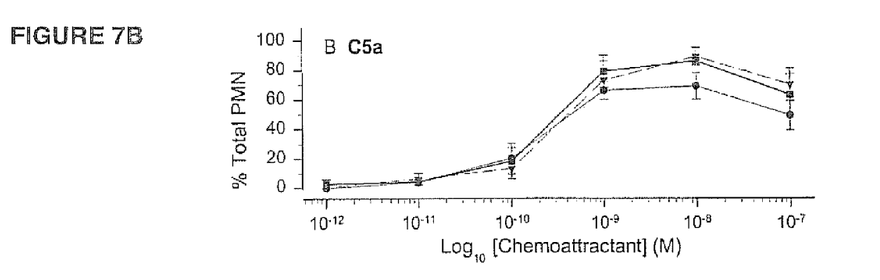

Not having to label the cells, in combination with an optimized micro-hole spacing, can also be used to reduce the detrimental effects of the transient nature of the chemical gradient formation. It is well known that Boyden chamber assays are associated with bell-shaped pharmacological response to a chemoattractant as is shown in FIGS. 7A and 7B which depict "agonist" bell-shaped curves observed with current commercially available Boyden chamber measurements. Shown is the number of cells undergoing chemotaxis (vertical axis) versus an increasing concentration of chemoattractant, IL-8 in FIG. 7A and C5a in FIG. 7B. Higher concentrations are non-optimum and can appear the same as inhibition effects one is trying to measure. It is anticipated that having a kinetic, homogenous assay read-out along with control of the spatial hole geometry will provide an enhanced ability to isolate this artifact. Data from [8] Frevert et al.

As chemoattractant "agonist" concentration is increased, one measures and increase in chemotactic response up to a maximum response. Increasing concentrations further causes the chemotactic signal to actually decrease. It is theorized that this is the result of an oversaturation of chemoattractant on the top side of the Boyden chamber, effectively confusing the cells and causing a muted response. This concentration and time-dependent effect makes determination of antagonist pharmacology very difficult, as slight deviations from the optimum "peak" of the agonist curve cannot be easily distinguished from those of a competitive antagonist which should also be inhibiting the response. It is our believe that having control of the spatial micro-hole density, using a kinetic, non-labeled read and homogeneous assay format will allow researchers to better control this effect and thereby provide more robust antagonist pharmacology.

Lastly, much like the design attribute of micro-fluidic channels, having the ability to directly view the cells during the chemotaxis process allows researchers to study morphological changes, and or associate the response to other imaging parameters for example the "shape change" associated with a migrating or invasive morphological phenotype. Aside from the phase contrast or DIC image, improved optical clarity will also improve, though not enable, the use of fluorescence probes. One salient example would be the combination of phase-sensitive imaging with fluorescent labels for sorting out the effects of mutant cell lines, or identifying different migration parameters for mixed cell lines. However, unlike the use of micro-fluidic channels, the invention presented here is easy to use, does not suffer from evaporation effects or shall chemical gradients.

Figure 8A:
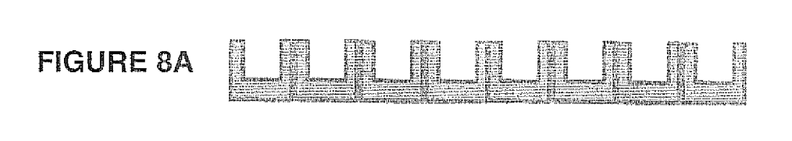
FIGS. 8A and 8B depict a side view and a top view of a preferred embodiment of the invention including a 96-well consumable comprised of 96 individual Boyden chambers using a laser photo-machined membrane.
Figure 8B:
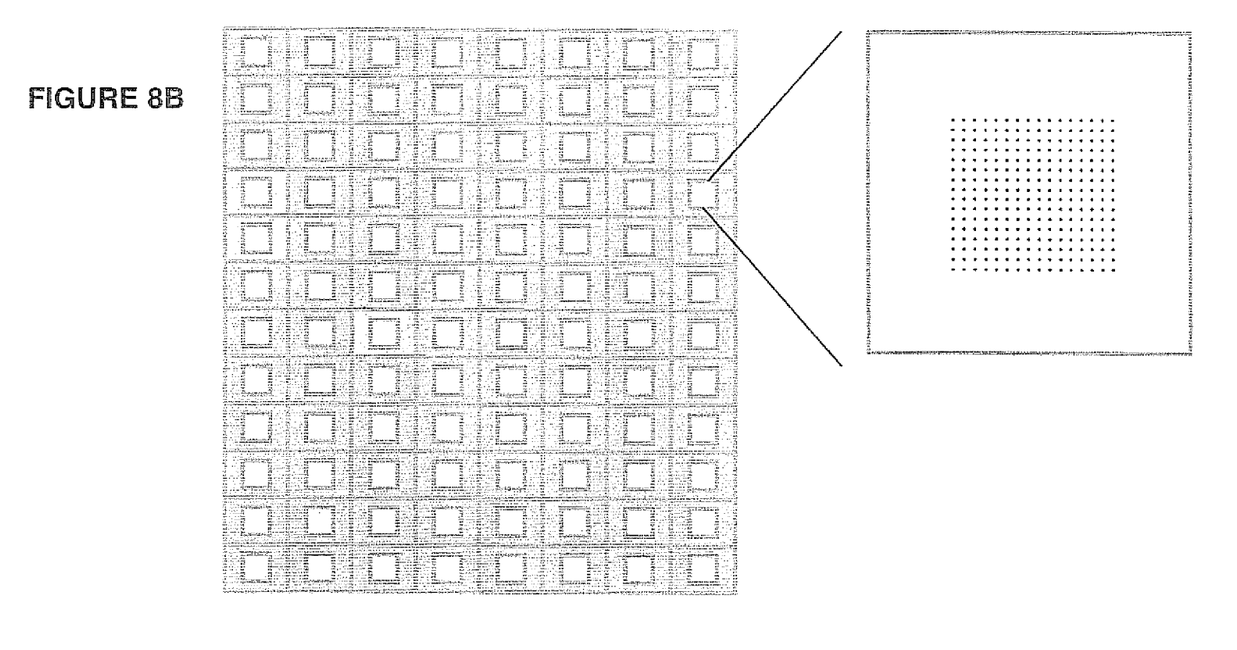
Figure 9A:
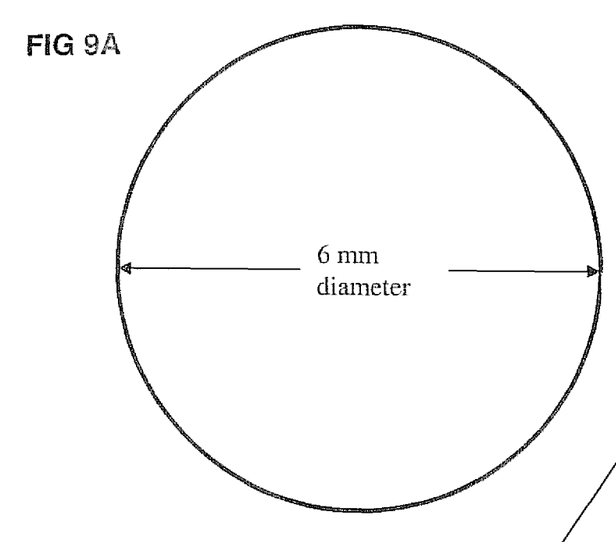
FIGS. 9A-9D show potential well geometries for reducing cell usage.
Figure 9B:
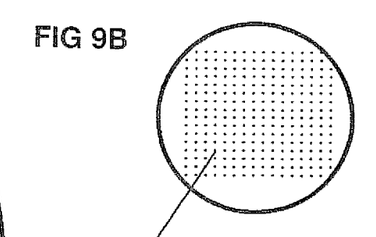
Figure 9C:
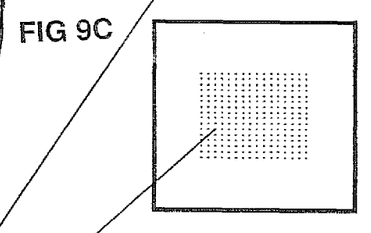
Figure 9D:
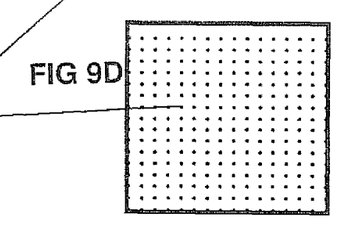

It should be understood, that the single-well geometry described in FIGS. 3, 4 and 5 can easily be extended to a rectangular array comprised of a plurality of wells and common formats used the biological sciences for example 6-well, 24-well, 96-well, 384-well and 1536 well geometries. An example of a 96-well format is depicted in FIG. 8A and FIG. 8B. Each of the individual wells would have its only two-dimensional grid of laser machined micro-pores. The commercial solutions previously described are generally found in 6-well, 24-well and 96-well formats. One of the design improvements in our invention is to be able to make a quantitative measurement using far fewer cells. To achieve this we could envision using a smaller reservoir dimension than those currently available as demonstrated with the examples shown in FIGS. 9A-9D. FIG. 9A shows individual well dimensions for a standard 96-well format. The standard 96-well format uses 6 mm diameter wells in a 12×8 format on 9 mm centers and is the highest format commercially available. A preferred embodiment of this invention would be to use smaller well dimensions so as to reduce cell usage required in current commercially available Boyden chamber systems. FIGS. 9B, 9C and 9D demonstrate different well geometries with different micro-hole patterns and densities. The individual wells shown could be placed on 9 mm centers to be consistent with a 96-well geometry, or could be utilized in a 384 well or higher density microplate format.

Although the invention described in this document is directed to a test chamber for measuring the migration of cells to chemical stimuli, e.g., chemotaxis or chemokinesis, the invention has applications beyond cell migration for example in the measurement of cell permeability, cell transport, cell invasion (others) where direct imaging of the surface would allow for non-invasive, quantitative assessment of the cells on the membrane in situ.

ALTERNATIVE EMBODIMENTS

Different types of polymers and polymer thicknesses, amenable to the laser ablation photo-machining may be used in accordance with the invention. Variations in pore size, pore density and pore location are also anticipated. It is anticipated that pore geometry and spacing will be used to enhance the gradient homogeneity at the top surface of the membrane. Various imaging systems could be used to image the membrane in situ, including epifluorescence, iZernike phase contrast, differential interference contrast (DIC), Hoffman modulation contrast and others. Different data processing schemes could also be utilized including measuring just the cells on the top side of the membrane, or alternatively measuring cells at three different planes being the a) top side of the membrane, b) bottom side of the membrane and at the bottom of the collection reservoir (lower chamber).

In order to reduce cell usage, many different potential reservoir configurations are possible, including moving to smaller reservoir formats, or smaller microplate formats such as a half-area 96-well format, 384-well format, or 1536-well format. Another alternative embodiment would be to apply biological coatings to the surface of the membrane such as collagen 1, fibronectin, or laminin. This type of coating would be a very thin molecular surface coating so as not to plug the microholes. It is also possible to apply a thicker extracellular matrix (ECM) coating to the membrane, where the Boyden chamber can be used to measure the ability of cells to invade the ECM, an assay known as a cell invasion assay. This is a natural extension and common use of existing Boyden chamber consumables.

There are several advantages of this invention over existing prior-art Boyden chamber devices. While much of this document has described the advantages for measurements of cell migration, many of these advantages are extendable to other applications for Boyden chambers. This, non-obvious modification, has several practical benefits:

a) Replacing the track-etch membrane of the Boyden chamber with one manufactured by laser ablation, enables for the first time in situ quantitative optical imaging methods such as inverted Zernike phase contrast, differential interference contrast (DIC) and Hoffman modulation contrast techniques to be used.

b) Cells no longer have to be exposed to potentially invasive, fluorescent labeling dyes or protocols. This is very important for primary cells which can be time-sensitive, or label sensitive. It also save operator time and reduces reagent cost.

c) Eliminating the use of fluorescent labels, and being able to count the cells in situ, removes the need for manual protocol steps such as scraping cells off either side of the membrane in order to separate the cells and count them. Using this invention, the assay can now be run in an automated, homogeneous format. The only existing homogeneous chemotaxis assay format, the Fluoroblok™ system sold by Becton Dickenson, relies on using fluorescent labels and is relatively expensive to comparable products.

d) Direct imaging of the cells on the surface of the membrane, without using fluorescent probes or optical stains greatly enhances the extension of these assays to a homogeneous, automated, multi-time point data collection and analysis. Morphological changes to the cells, such as shape change or actin polymerization can be monitored in situ. In addition, direct cell imaging on the membrane allows for other the measurement of individual cell-based parameters not possible with current Boyden chamber solutions. Individual cell migration and invasion assays parameters such as a) speed and b) persistence of migration can be monitored kinetically.

e) Existing commercially available Boyden chamber solutions dictate that at least 50,000 to 100,000 cells are required per measurement well to achieve reasonable measurement precision. This invention enables, for the first time, control of the pore size, spacing and location. Using these design attributes, along with an optimized upper reservoir capacity will allow for similar assay precision using only a few thousand cells.

f) Laser-based photo-machining of the membrane allows precise control of both the pore size, pore spacing and pore location, enabling, for the first time, the ability to use these parameters to optimize the chemical gradient formation process when used as a chemotaxis or chemo-invasion measurement device. It is anticipated, that combing this feature with a kinetic read-out of the cell migration process, e.g. with an automated microscope such as the IncuCyte™ (Essen BioScience, Ann Arbor Mich.), that the assay system will provide more stable pharmacological data and reduce the artifactual effects of agonist roll-over as depicted in FIGS. 7A and 7B, and the potential confusion in measuring antagonist inhibition in these types of assays.

REFERENCES

1.) Stephen Boyden, Ph.D., "The Chemotactic Effect of Mixtures of Antibody and Antigen on Polymorphonuclear Leucocytes" *J. Exp. Med.* 115: pp. 453-466, (1962).

2.) J. A. Quinn, J. L. Ajnderson, W. S. Ho, and W. J. Petzny, J., Model Pores of Molecular Dimension, the Preparation and Characterization of Track-Etched Membranes, *Biophysical Journal Volume* 12, (1972)

3.) Pamela Zengel, Anna Nguyen-Hoang, Christoph Schildhammer, Roman Zantl, Valentin Kahl, Elias Horn, "u-Slide Chemotaxis: A new chamber for long-term chemotaxis studies" *BMC Cell Biology* 12:21, (2011)

4.) Ivar Meyvantsson, Elizabeth Vu, Casey Lamers, Daniella Echeverria, Tracy Worzella, Victoria Echeverria, Allyson Skoien, Steven Hayes, "Image-based analysis of primary human neutrophil chemotaxis in an automated direct-viewing assay", *Journal of Immunological Methods*, (2011 in press).

5.) Suparna Sanyal, Susan Qian, Jeff Partridge and Marhsall Kosovsky, "Optimized Chemotaxis Conditions for Primary Blood Monocytes or THP-1 Cells using BD Falcon™ FluoroBlok™ 96-Multiwell Insert Plates, *Technical Bulletin #457, BD Biosciences*, BD Biosciences-Discovery Labware, Bedford, Mass. 01730

6.) U.S. Pat. No. 6,488,829 Issued Dec. 3, 2002: Inventors: Schroeder; Kirk S. (Ann Arbor, Mich.), Neagle; Bradley D. (Ann Arbor, Mich.) High-throughput electrophysiological measurement apparatus.

7.) U.S. Pat. No. 6,270,730 Issued Sep. 18, 2007: Inventors: Schroeder; Kirk S. (Ann Arbor, Mich.), Neagle; Bradley D. (Ann Arbor, Mich.) High-throughput electrophysiological measurement system.

8.) C. W. Frevert, V. A. Wong, R. B. Goodman, R. Goodwin, T. R. Martin, "Rapid fluorescence-based measurement of neutrophil migration in vitro, *Journal of Immunological Methods* 213 (1998) 41-52.

The invention claimed is:

1. Biological measurement apparatus, comprising:
a bottom reservoir;
a top reservoir;
a thin porous membrane separating the top and bottom reservoirs; and wherein:
the pores of the membrane are formed using a laser-based photo-machining (ablation) process; and
the porous membrane is optically clear and devoid of patterned electrodes and significant optical phase perturbations, thereby enabling quantitative, phase-contrast optical imaging of biological cells on the membrane without the use of fluorescent probes or optical staining.

2. The apparatus of claim 1, wherein the membrane is composed of polyethylene terephthalate (PET).

3. The apparatus of claim 1, wherein the membrane is composed of polycarbonate.

4. The apparatus of claim 1, wherein the membrane is composed of polyimide.

5. The apparatus of claim 1, wherein the membrane is composed of polyether ether ketone (PEEK).

6. The apparatus of claim 1, wherein the pores of the membrane have diameters in range of 1 to 15 microns.

7. The apparatus of claim 1, wherein the pores of the membrane are spaced apart at a distance ranging from 10 to 200 microns.

8. The apparatus of claim 1, further including a plurality of upper and lower reservoirs forming a multi-well plate.

9. The apparatus of claim 1, wherein the membrane is coated with collagen 1, fibronectin, laminin or other extracellular matrix.

10. The apparatus of claim 1, wherein the reservoirs are manufactured with an injection molded plastic.

11. The apparatus of claim 1, wherein the membrane is attached to either the top or bottom reservoir using an ultrasonic welding process or chemical bonding agent.

12. The apparatus of claim 1, wherein the membrane is attached to the bottom surface of the top reservoir thereby forming a removable insert that fits inside the bottom reservoir.

13. The apparatus of claim 1, where a plurality of upper reservoirs are attached to a porous membrane, the assembly of which forms a removable insert that fits inside a plurality of co-aligned bottom reservoirs forming a microplate.

14. A biological measurement system, comprising:
a bottom reservoir;
a top reservoir;
a thin porous membrane separating the top and bottom reservoirs, with the pores of the membrane being formed using a laser-based photo-machining (ablation) process such that the porous membrane is optically clear and devoid of significant optical phase perturbations; and
a phase contrast imaging system for performing quantitative optical imaging of biological cells on the membrane without the use of fluorescent probes or optical staining, the phase contrast imaging system including a light source disposed on one side of the membrane and an imaging detector disposed on the other side of the membrane.

15. The biological measurement system of claim 14, wherein the phase contrast imaging system utilizes one of Zernike phase contrast, differential interference contrast (DIC) or Hoffman modulation contrast.

16. The biological measurement system of claim 14, wherein the membrane is composed of polyethylene terephthalate (PET).

17. The biological measurement system of claim 14 wherein the membrane is composed of polycarbonate.

18. The biological measurement system of claim 14, wherein the membrane is composed of polyimide.

19. The biological measurement system of claim 14, wherein the membrane is composed of polyether ether ketone (PEEK).

20. The biological measurement system of claim 14, wherein the pores of the membrane have diameters in range of 1 to 15 microns.

21. The biological measurement system of claim 14, wherein the pores of the membrane are spaced apart at a distance ranging from 10 to 200 microns.

22. The biological measurement system of claim 14, further including a plurality of upper and lower reservoirs forming a multi-well plate.

23. The biological measurement system of claim 14, wherein the membrane is coated with collagen 1, fibronectin, laminin or other extracellular matrix.

24. The biological measurement system of claim 14, wherein the reservoirs are manufactured with an injection molded plastic.

25. The biological measurement system of claim 14, wherein the membrane is attached to either the top or bottom reservoir using an ultrasonic welding or chemical bonding process.

26. The biological measurement system of claim 14, wherein the membrane is attached to the bottom surface of the top reservoir thereby forming a removable insert that fits inside the bottom reservoir.

27. The biological measurement system of claim 14, where a plurality of upper reservoirs are attached to a porous membrane, the assembly of which forms a removable insert that fits inside a plurality of co-aligned bottom reservoirs connected together.

* * * * *